(12) United States Patent
Trahan et al.

(10) Patent No.: US 10,744,475 B1
(45) Date of Patent: Aug. 18, 2020

(54) METHANOL PRODUCTION REACTOR APPARATUS AND METHOD OF OPERATIONS USING HOMOGENEOUS CATALYST

(71) Applicants: David O. Trahan, Lafayette, LA (US); Srinivasan Ambatipati, Lafayette, LA (US)

(72) Inventors: David O. Trahan, Lafayette, LA (US); Srinivasan Ambatipati, Lafayette, LA (US)

(*) Notice: Subject to any disclaimer, the term of this patent is extended or adjusted under 35 U.S.C. 154(b) by 0 days.

(21) Appl. No.: 16/785,253

(22) Filed: Feb. 7, 2020

Related U.S. Application Data

(60) Provisional application No. 62/803,224, filed on Feb. 8, 2019.

(51) Int. Cl.
| | | |
|---|---|---|
| *B01J 10/00* | (2006.01) | |
| *C07C 29/152* | (2006.01) | |
| *B01J 4/00* | (2006.01) | |
| *B01J 19/00* | (2006.01) | |
| *B01D 5/00* | (2006.01) | |
| *B01D 3/06* | (2006.01) | |

(52) U.S. Cl.
CPC .............. *B01J 10/002* (2013.01); *B01D 3/06* (2013.01); *B01D 5/006* (2013.01); *B01J 4/004* (2013.01); *B01J 19/0013* (2013.01); *C07C 29/152* (2013.01); *B01J 2219/00083* (2013.01); *B01J 2219/00094* (2013.01); *B01J 2219/00182* (2013.01)

(58) Field of Classification Search
CPC ...... B01J 10/002; B01J 4/004; B01J 19/0013; B01J 2219/00083; B01J 2219/00094; B01J 2219/00182; C07C 29/152
See application file for complete search history.

(56) References Cited

U.S. PATENT DOCUMENTS

| | | |
|---|---|---|
| 1,302,011 A | 4/1919 | Christiansen |
| 1,868,096 A | 7/1932 | Dreyfus |
| 3,888,896 A | 6/1975 | Espino et al. |
| 4,031,123 A | 6/1977 | Espino et al. |
| 4,235,799 A | 11/1980 | Wentworth et al. |
| 4,346,179 A | 8/1982 | Sugier et al. |
| 4,567,204 A | 1/1986 | Mednick et al. |
| 4,628,066 A | 12/1986 | Bonnell et al. |
| 4,766,154 A | 8/1988 | Bonnell et al. |
| 5,179,129 A | 1/1993 | Studer |
| 6,881,759 B2 | 4/2005 | Nielsen et al. |
| 8,968,685 B2* | 3/2015 | Hawkins ............... C10K 1/004 422/630 |

FOREIGN PATENT DOCUMENTS

CA     1157053     11/1983

* cited by examiner

*Primary Examiner* — Lessanework Seifu
(74) *Attorney, Agent, or Firm* — Matthews, Lawson, McCutcheon & Joseph, PLLC

(57) ABSTRACT

A system and method of continuous production of methanol is disclosed utilizing enriched syngas and a homogenous liquid catalyst comprising an organo-nickel compound, an ether solvent, and an organic methoxide salt. The syngas is directed into a reaction chamber in such a way as to maximize the gas-liquid interface (e.g., an eductor nozzle or bubble column) while two condensers receive tail gas and reactant fluid from the reaction chamber, the latter after undergoing flash separation. Liquid catalyst is recovered and recycled back into the system via the second condenser.

12 Claims, 1 Drawing Sheet

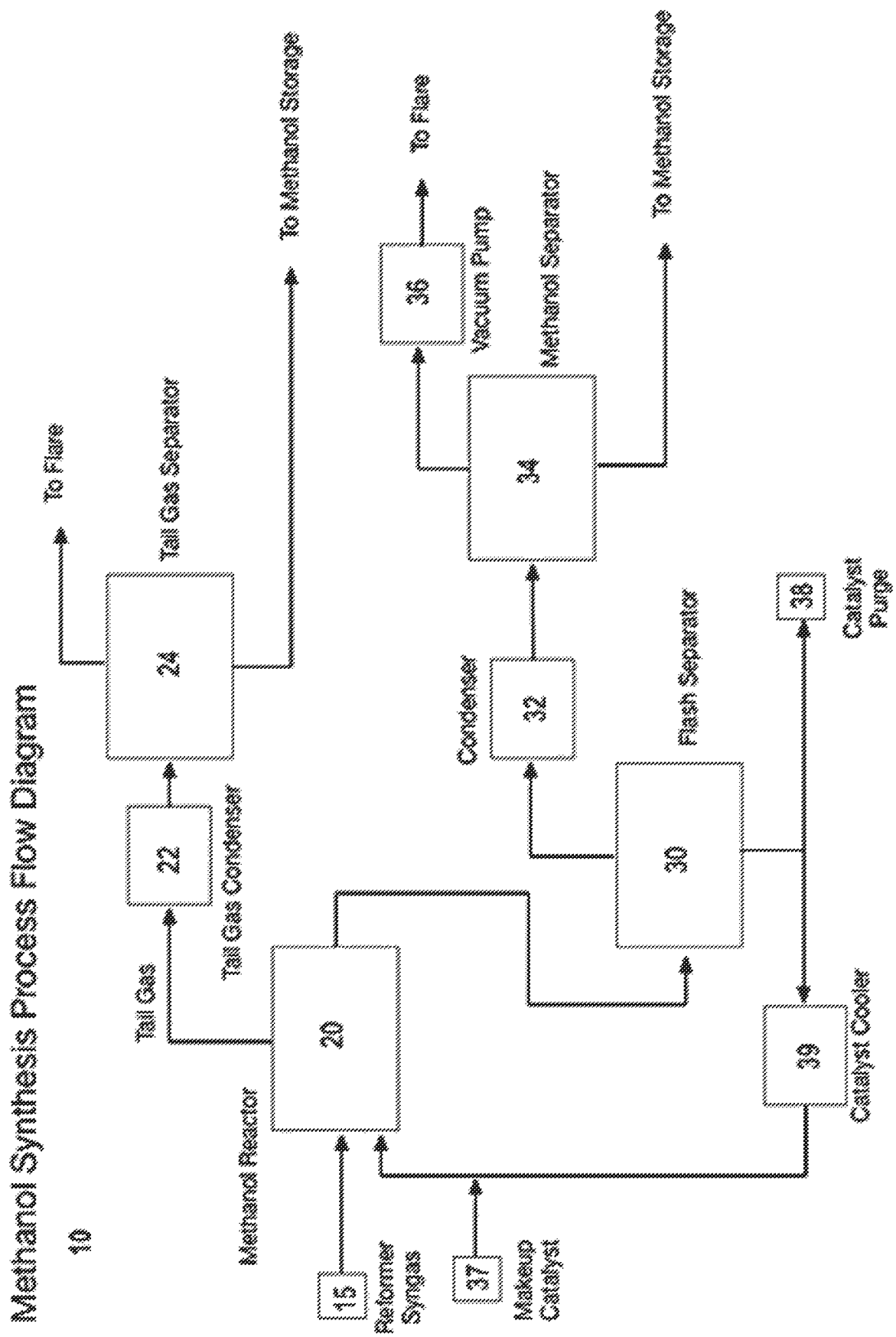

METHANOL PRODUCTION REACTOR APPARATUS AND METHOD OF OPERATIONS USING HOMOGENEOUS CATALYST

PRIORITY

This application claims the benefit of and priority to U.S. Provisional Application No. 62/803,224, filed 8 Feb. 2019, by David Trahan and Srinivasan Ambatipati, entitled "Methanol Production Reactor Apparatus and Method of Operation Using a Homogenous Catalyst." The disclosure of this provisional application is herein incorporated by reference.

FIELD

The present invention is a novel improvement over other methods and apparatus for the production of methanol from synthesis gas ("syngas") feed containing carbon monoxide, hydrogen, nitrogen, carbon dioxide along with trace amounts of other gases. In its basic description, the process directs properly conditioned synthesis gas through a conduit into a vertical pressure vessel, also called a bubble column reactor, containing a concentration of a homogenous liquid catalyst diluted in a liquid polyglycol and methanol solvent which is capable of producing the conversion of syngas into methanol, and methanol derivatives. The process operates in a continuous gas flow up to 21 Bar (300 psi) and temperatures less than 121° C. (250° F.). The syngas composition is preferred to be a 2:1 hydrogen to carbon monoxide ratio concentration with less than 50 parts per million water and less than 100 parts per million carbon dioxide. A small volume of syngas-containing gas is exhausted out the top of gas to methanol reactor and travels through a backpressure gas regulator that controls the reaction pressure within the vessel. The continuous flow of residual syngas gas is directed through a line into a gas scrubber and then to a flare or catalytic high temperature thermal oxidizer.

BACKGROUND OF INVENTION

The production of methanol and methanol derivatives is a well-known process in the chemical production industry. There are published methods using solid catalyst, heterogenous slurry catalyst and homogenous liquid catalyst. Over 95 percent of methanol produced today involves the use of a Fischer-Tropsch ("F-T") type solid catalyst in a reactor vessel of a particular style including: a packed bed catalyst arrangement, tubular catalyst arrangement or micronized solid particles of F-T catalyst in a slurry form carried in an organic or inorganic solvent.

This novel invention takes particular advantage of a highly efficient homogenous liquid methanol producing catalyst for producing methanol directly from syngas containing carbon monoxide, hydrogen, nitrogen, carbon dioxide and trace amount of other gases including methane. More particularly this invention describes reacting syngas in the presence of a homogenous liquid catalyst inside a novel bubble column reactor.

Methanol is a valuable chemical intermediate and fuel product. The growing demand for energy products in a safe liquid form makes the production of methanol a valuable energy resource. Methanol production processes use syngas containing mainly hydrogen and carbon monoxide as a gaseous feedstock to produce methanol product.

Syngas is a common name given to a gas mixture that contains varying amounts of hydrogen and carbon monoxide. Examples of production methods include steam reforming of natural gas or liquid hydrocarbons to produce hydrogen, the gasification of coal, biomass, and in some types of waste-to-energy gasification facilities. The name comes from their use as intermediates in creating synthetic natural gas and for producing ammonia or methanol.

Gasification is a thermochemical pyrolytic process that converts carbonaceous materials, such as coal, petroleum, biofuel, or biomass, into carbon monoxide and hydrogen by reacting the raw material, such as house waste, or compost at high temperatures with a controlled amount of oxygen and/or steam. The resulting gas mixture is called syngas.

The advantage of gasification is that using the syngas is potentially more efficient than direct combustion of the original fuel because it can be combusted at higher temperatures or even used in fuel cells, so that the thermodynamic upper limit to the efficiency defined by Carnot's rule is higher or not applicable. Syngas may be burned directly in internal combustion engines, used to produce methanol and hydrogen, or converted via the Fischer-Tropsch process into synthetic fuel. Gasification can also begin with materials that are not otherwise useful fuels, such as biomass or organic waste. In addition, the high-temperature combustion refines out corrosive ash elements such as chloride and potassium, allowing clean gas production from otherwise problematic fuels.

Gasification relies on chemical processes at elevated temperatures >700° C. (>1290° F.), which distinguishes it from biological processes such as anaerobic digestion that produce biogas.

Depending upon the specific method of producing syngas the ratio of hydrogen to carbon monoxide will vary. The reaction to produce methanol generally requires a hydrogen to carbon monoxide ratio of at least 2 to 1. The reference to a hydrogen to carbon monoxide ratio describes how the syngas contains a minimum of 2 moles of hydrogen for every mole of carbon monoxide. To achieve a minimum of a 2 to 1 ratio of hydrogen to carbon monoxide syngas may be conditioned through the use of a water gas shift reaction.

The water-gas shift reaction is a chemical reaction in which carbon monoxide reacts with water vapor to form carbon dioxide and hydrogen:

$$CO + H2O \rightarrow CO2 + H2$$

The water-gas shift reaction is an important reaction step in the production of syngas for use in methanol production. It is also often used in conjunction with steam reforming of methane or other hydrocarbons, for the production of high purity hydrogen for use in ammonia synthesis.

Syngas produced from wood or biomass gasification or pyrolysis possesses a typical hydrogen to carbon monoxide molar ratio of 1 to 1. Therefore, syngas conditioning to increase the molar concentration of hydrogen is necessary. In this case a water gas shift reaction is used to increase the hydrogen concentration.

Syngas production is commonly found using hydrocarbon or natural gas as the primary carbon source. There are many sources of natural gas located in isolated regions which are far from pipeline access. Natural gas co-produced with crude oil is typically partially consumed locally to produce heat for process equipment, electricity for local needs and in some cases can be re-injected with a gas compressor into the oil bearing formation to maintain geological formation pressures. More typically it is simply burned in a thermal flare allowing the oil production company the ability to produce a greater volume of crude oil.

Methanol can be produced from any carbon-based source. These would include: natural gas, coal, municipal wastes, landfill gas, wood wastes, aquatic and subaquatic biomass. Methanol is primarily produced by steam-reforming natural gas to create a syngas which is fed into a reactor vessel in the presence of a nickel catalyst to produce water vapor and methanol. A distillation step is used to remove water from the finished methanol.

Methanol is considered a portable source of energy. About 34 percent of the input gas (energy) is lost in its synthesis so its production away from markets requires very cheap natural gas supply to be viable for large volume production systems. Transport costs impact heavily on its viability. There are many reasons why methanol is an important key to a syngas-based fuels and chemical industry. First, methanol is synthesized in over 99% or greater selectivity, in sharp contrast to the wide array of other hydrocarbon products, from methane to waxes, obtained in the Fischer-Tropsch (F-T) reaction. Second, the weight retention of syngas ($2H_2$: $1CO$) as a feedstock for methanol is 100%. Syngas is a costly raw material for the production of hydrocarbons obtained in the F-T reaction where oxygen is eliminated as water or $CO_2$. Third, methanol furnishes selective pathways to a number of important chemicals, including formaldehyde and the widely used two carbon oxygenated chemicals. This route to fuels and to two carbon chemicals from methanol is more attractive than the direct synthesis from syngas.

For over many years, new increases in methanol production capacity have been driven by countries with large oil and/or natural gas reserves, building methanol facilities as a way to transport and monetize "stranded gas" resources. Little new capacity has been based on byproduct growth. Generally, systematic rationalization has followed at a pace similar to expansion, particularly in the high-cost natural gas-based areas like North America and Europe.

Globally methanol production capacity stands at between 40 and 50 million metric tons per year (approximately 14 to 15 billion gallons). The operating methanol production plants in the United States have greatly reduced capacity given the much higher cost of natural gas used in the production of methanol. Total demand for methanol in the United States is over 8 million metric tons (2.6 billion gallons), with United States based production satisfying only approximately 5 percent of this demand, with imports mainly from Trinidad, Chile, Venezuela, Equatorial Guinea and Canada making up the remaining supply. Generally, one metric ton of methanol equals 333 gallons.

In the United States and other parts of the world, smaller and more regional resources for syngas production are available. In 2013 the National Renewable Energy Laboratory ("NREL") reported that it estimated 7.9 million metric tons a year of methane generation potential for selected biogas sources in the United States, including: wastewater, landfills, animal manure, IIC organic waste. This is equal to about 420 billion cubic feet or 431 trillion British thermal units ("BTU"). According to a 2013 report by the Energy Information Association, this amount of energy produced from biogas could displace about 5% of current natural gas consumption in the electric power sector and 56% of the natural gas consumption in the transportation sector. The availability of low cost or stranded natural gas in the U.S. is growing. Many areas of development lack pipeline infrastructure to transport the natural gas to a market. Those isolated sources of natural gas that do have pipeline infrastructure available earn sub market value for their product due to the high cost of pipeline transmission to a consumption point.

In the case of biomass to methanol the concept of transporting biomass to a centralized, large scale methanol production plant is uneconomical. If biomass is transported a distance of 100 miles or greater the cost of transportation raises the cost of the biomass to uneconomical cost levels for the conversion into methanol.

In both the case of stranded or isolated natural gas, as with biomass resources, there exists a real need for a small scale (micro-plant) methanol production process capable of using the regional natural gas, biomass or other carbon based resources available. Once produced into a methanol product the regional market can take advantage of the regionally produced methanol product as opposed to sourcing the product from a distant, many times foreign source for the product. The novel invention provides a small, modular, micro-plant option for energy companies.

In contrast, today all commercial methanol process plants operating are constructed on a very large scale, high volume production basis. A typical methanol process plant today is constructed with capacities ranging from 1,000 to 5,000 metric tons per day (333,000 up to 1,665,000 gallons per day). The micro-plant methanol production reactor is constructed with a capacity ranging from 0.5 to 30 tons per day (166 to 10,000 gallons per day). The current F-T commercial process systems available today are unable to reach these low capacities of production economically.

Various methods have been developed for the production of methanol from gas mixtures containing carbon monoxide, hydrogen and carbon dioxide, among these are:

U.S. Pat. No. 6,881,759 discloses a process for methanol production in a liquid phase reactor from a synthesis gas comprising of hydrogen, carbon dioxide, and carbon monoxide. The liquid phase reactor contains a solid catalyst suspended in methanol. In this invention the methanol acts both as a product and as a suspension medium for the catalyst. A part of the methanol in the reactor is withdrawn from the reactor in the form of methanol product.

U.S. Pat. No. 5,179,129 discloses a process to produce methanol from syngas comprising of hydrogen, carbon monoxide and carbon dioxide in a two-stage liquid phase reactor system. Each reactor is operated at optimum temperature range to maximize methanol productivity, and once through product conversion of 9.1 moles methanol per 100 moles of syngas can be achieved.

U.S. Pat. No. 4,766,154 discloses a process for the production of methanol from a syngas feed containing carbon monoxide, carbon dioxide and hydrogen. The process described is a combination of two liquid phase methanol reactors into a staging process, such that each reactor is operated to a favor of a particular reaction mechanism. The first reactor is controlled to favor the hydrogenation of carbon monoxide, and the second reactor is controlled to favor the hydrogenation of carbon dioxide.

U.S. Pat. No. 4,628,066 discloses a process for increasing the capacity of a gas phase synthesis loop for the production of methanol from a syngas feed. The syngas feed is initially passed to a liquid phase methanol reactor to convert a portion of the syngas to methanol or methanol and higher aliphatic alcohols. The mixture is subsequently cooled to condense and recover the methanol and/or higher alcohols. The unreacted syngas is passed to a gas phase synthesis loop for further conversion and recovery of methanol.

U.S. Pat. No. 4,567,204 discloses a process for the production of methanol in a liquid phase methanol reactor by entraining a methanol forming catalyst in an inert liquid and contacting the entrained catalyst with a synthesis gas comprising of carbon monoxide and hydrogen.

U.S. Pat. No. 4,346,179 discloses a process for producing methanol and its higher homologs from a synthesis gas containing essentially carbon dioxide, carbon monoxide, and hydrogen. A synthesis gas is treated in a first catalytic reaction zone at 230-350° C. The effluent from the first catalytic reaction zone is cooled and condensed and as a gas fraction is separated from the liquid condensate. The gas fraction is subsequently treated at 240-300° C. in a second catalytic reaction zone to produce a liquid methanol fraction. The liquid methanol fraction is subsequently admixed with the liquid condensate to form a gasoline constituent product.

U.S. Pat. No. 4,235,799 discloses a process for producing methanol by passing a mixture of hydrogen and one or more carbon oxides into contact with at least two beds of catalyst arranged in series. The catalyst beds are operated at increasing temperature levels in the direction of flow of the mixture. The mixture is subsequently cooled by indirect heat exchange and passed into contact with at least further bed of catalyst.

U.S. Pat. No. 4,031,123 discloses a similar method for preparing methanol with the improvement that paraffinics and cycloparaffinnics are used as the inert hydrocarbon liquid which the catalyst bed is in contact.

U.S. Pat. No. 3,888,896 discloses a process for producing methanol from carbon monoxide and hydrogen by saturating an inert organic liquid medium, such as pseudocumene, with carbon monoxide and hydrogen and contacting the saturated liquid medium with methanol forming catalyst such as those containing zinc and chromium.

U.S. Pat. No. 1,868,096 discloses a process for producing methanol by passing a reaction gas mixture under the request conditions of temperature and pressure initially over one or more catalyst masses composed of zinc oxide or zinc oxide and chromium oxide and subsequently passing said mixture over one or more methanol catalysts sensitive to sulfur poisoning such as catalysts comprising of copper, manganese or compounds of copper or manganese. The reaction gases are passed successively through a number of reactor vessels arranged in series as an open system.

Canadian Pat. No. 1,157,053 discloses a liquid phase methanol synthesis process wherein methanol is produced by contacting a synthesis gas comprising hydrogen and carbon monoxide with a catalyst in presence of an inert liquid. The catalyst in contact with the inert liquid is in the form of particles of a size less than about 125 microns.

U.S. Pat. No. 1,302,011 discloses a invention relates to a method of producing methyl alcohol from alkyl formates by treating an alkyl formate with hydrogen in the presence of an appropriate catalyzer to decompose the formate whereby methyl alcohol and the alcohol derived from the alkyl contained in the alkyl formate in question is formed.

Existing processes using 2 to 1 syngas to produce methanol operate at far greater pressure and temperatures. The inventors are unaware of any existing methanol production process system which use low pressure syngas and low reaction temperatures using a homogenous type catalyst to produce methanol in commerce.

SUMMARY OF INVENTION

The present invention is an improved method and apparatus for the production of methanol from synthesis gas containing hydrogen and carbon monoxide in a 2:1 concentration ratio, along with trace amounts of other gases. The process directs conditioned synthesis gas into a vertical bubble column reactor in one or more locations. The vessel contains a volume of an alkaline polyol and alcohol solvent with a homogenous liquid catalyst capable of causing a gas to methanol reaction with continuous gas flow at mild pressure and temperature conditions. The continuous flow of residual gas out of the gas-to-methanol reactor is controlled by a back-pressure regulator which controls the process reaction pressure. The liquid inside the vessel is continuously circulated through a fan assisted cooling radiator to control the exothermic reaction temperature created when methanol is produced. A volume of the liquid in the vessel is continuously removed and pumped into a second pressure vessel where a portion of the methanol in solution is flash separated from the liquid before it is returned to the reactor vessel.

Various embodiments of the disclosure are discussed in detail below. While specific implementation are discussed, it should be understood that this is done for illustration purposes only. A person skilled in the art will recognize that the other components and configurations may be used without departing from the scope of the disclosure.

DRAWINGS

FIG. 1 depicts an embodiment of a process flow chart for a methanol synthesis system and method in accordance with the present disclosure.

DETAILED DESCRIPTION

Before describing selected embodiments of the present disclosure in detail, it is to be understood that the present invention is not limited to the embodiments described herein. The disclosure and description herein is illustrative and explanatory of one or more presently preferred embodiments and variations thereof, and it will be appreciated by those skilled in the art that various changes in the design, organization, order of operation, means of operation, equipment structures and location, methodology, and use of mechanical equivalents may be made without departing from the spirit of the invention.

As well, it should be understood the drawings are intended to illustrate and plainly disclose presently preferred embodiments to one of skill in the art, but are not intended to be manufacturing level drawings or renditions of final products and may include simplified conceptual views as desired for easier and quicker understanding or explanation. As well, the relative size and arrangement of the components may differ from that shown and still operate within the spirit of the invention.

Moreover, it will be understood that various directions such as "upper," "lower," "bottom," "top," "left," "right," and so forth are made only with respect to explanation in conjunction with the drawings, and that the components may be oriented differently, for instance, during transportation and manufacturing as well as operation. Because many varying and different embodiments may be made within the scope of the concept(s) herein taught, and because many modifications may be made in the embodiments described herein, it is to be understood that the details herein are to be interpreted as illustrative and non-limiting.

As used in the present disclosure, "circulating" means agitating, blending or mixed of one or more fluids. "Coupled" is defined as connected, whether directly or indirectly through intervening components and is not necessarily limited to physical connections. Coupled devices may be devices which are in signal communications with one another. "Connected" means directly connected or indirectly connected. "Homogenous" means soluble in solution. "Homogenous catalysis" is a catalytic reaction where the catalyst is in the same phase as the reactants.

The present invention is an improvement over existing methanol production methods. The invention is a low pressure, low temperature, continuous syngas flow reactor for the production of methanol in a liquid reactor. In the inventive process, a liquid catalyst is preferably a homogenous liquid mixture of an organo-nickel compound, an ether solvent, an organic methoxide salt and methanol. The process takes advantage of the difference between the vapor pressure of the methanol and the vapor pressure of the balance of the liquid elements within the homogenous catalyst. The process additionally takes advantage of the ability of the liquid homogenous catalyst to function effectively in the presence of low to high concentrations of nitrogen. In an embodiment, the syngas production can utilize air as its primary source of oxygen, but preferably uses an enriched air or minimum 90 percent oxygen concentration. Syngas production by using regular air as the source of oxygen is much lower in cost as the capital and operational costs associated with a separate oxygen production but brings the disadvantage of a large volumetric increase in the nitrogen concentration which is an inert non-reactive gas requiring considerably larger process equipment for a given volume of natural gas processed. In the methanol reaction the nitrogen is an inert gas and does not participate in the reaction. If regular air, not enriched air, were used to produce syngas the nitrogen would represent the major portion of the tail gas leaving the gas distributor and would require scrubbing to remove methanol from the tail gas.

Accordingly, the invention is in its broadest aspect a process for producing methanol from a syngas containing carbon monoxide, hydrogen, carbon dioxide, nitrogen and trace amount of methane by steps of: passing specified syngas into a reactor containing a liquid homogenous methanol conversion catalyst in a solvent blend of polyol ether, organic alkoxide, and methanol.

In at least one embodiment of the present invention, the process involves reacting the syngas in the liquid homogenous methanol conversion catalyst, where methanol being formed is part of the liquid phase.

Turning now to FIG. 1, a flow diagram of an embodiment of the process 10 shows syngas 15 from reformer/conditioning section is directed to methanol reactor vessel 20 through a gas sparger. In an embodiment, the syngas is directed at a pressure between 10-17 bars (150-250 psi or 1,000-1,700 kPa) and a temperature between 100° C. and 200° C. (212° and 392° F.). The catalyst solution flows co-currently to syngas flow and maintains uniform reactor temperature.

Syngas 15 reacts in the presence of catalyst in the methanol reactor vessel 20 to produce methanol. In an embodiment, the rate of chemical reaction and fluid flow in reactor vessel 20 is controlled by level sensors; as the level of liquid in the reactor vessel rises due to the production of methanol liquid from syngas, it activates a pump to transfer a portion of the reaction fluid containing methanol product to a flash separator 30 which removes a portion of the methanol product and thereby controlling the liquid levels in the reactor vessel 20.

In an embodiment of the present invention, the syngas enters the reactor vessel 20 through one or more nozzles penetrating the wall of the reactor vessel 20 into the inner regions of the vessel in the lower half of the length of the vessel. The syngas nozzle can be connected to an internal pipe assembly which further directs the syngas into one or more eductor nozzles, which distribute the syngas and agitate the liquid within the reactor to increase gas-liquid contact.

In another embodiment of the of the present invention, a device such as a perforated conduit, a microporous metal or ceramic tube, or a glass or ceramic bead packed cylinder may be used in the reactor vessel 20 to create micro-bubbles in order to produce a large volume of gas bubbles increasing the overall gas to liquid surface area increasing the overall efficiency of the gas-liquid contact and reaction rate.

Traditionally, bubble fields have been generated using one of two techniques. The first technique is to drill a discrete hole in a non-porous material. Electro-discharge Machines, EDMs, have been used to drill holes with diameters as small as 22 microns and laser drills can drill holes with diameters on the order of 150 microns. The smallest conventional ANSI drill bit is a #80 which has a diameter of 342.9 microns.

The second technique is to use a porous inorganic material which allows the passage of gaseous material. Several industrial sources describe how porous materials can be generated in a number of ways. Porous metal structures are created from powdered metals or fine metal fibers. These materials are formed into a shape and sintered (sintered—to cause to become a coherent mass by heating without melting). In a similar manner alumina and silica powders can be sintered to generate porous ceramic structures. Larger pore ceramic or porous rock devices can be generated by increasing the grain size of the base materials. These types of porous materials can have effective pore diameters from submicron size to a hundred or more microns.

As stated previously, there is a range of overlap between the hole diameters generated by the two bubble generation techniques. However, the two techniques are distinguished by more than the size of the holes. Discrete drilled holes provide individual bubbles or bubble fountains depending on the diameter of the hole and the differential pressure applied across the hole. At very low differential pressures, individual bubbles are created at or near the surface of the material/liquid. As the differential pressure is increased, a fountain effect moves bubble generation away from the surface of the material. The interaction between discrete holes driven with high differential pressures and/or flow of the liquid can create complex bubble fields. Another principle difference between the bubble generation techniques is the range of hole diameters. For discrete holes in rigid materials, the range of hole diameters is limited by the nominal diameters of the drilling technique used and the machining tolerances. Although porous materials are quite often quoted as having a pore (i.e. a hole) diameter, the reality is that porous materials have a distribution of pore diameters. The distribution of pore sizes is a function of the distribution of the base materials the porous material is made from and the manufacturing technique used to create the porous material. Unlike discrete holes, porous materials tend to generate bubbles at all points along the material/liquid interface with the bubbles being generated at or very near the material/liquid interface regardless of the differential pressure applied. These features of porous materials can be used to infill the bubble field between discrete holes and generate bubbles with a range of small diameters. These small bubbles combined with the larger bubbles created using discrete holes provide a large diversity of bubble diameters.

In an embodiment, the present invention makes use of the bubble generating capacity of porous metal and/or porous ceramic devices. The porous wall material preferably has effective pore diameters less than 400-microns and more preferably in the 50 to 200-micron range. The effective diameter of the discrete holes is preferably greater than 300-microns and more preferably on the order of 1000 to 2000-microns.

There are many manufacturers of porous products that, while not specifically advertised for bubble making, could be adapted for that purpose. Engineering issues considered in selecting a porous material would include flow impedance, flow capacity, mechanical stability and cost.

In another embodiment of the present invention, the process combines the fluid agitation effect of an internal gas-liquid eductor assembly with a syngas micro-bubble dispersion serves to maximize gas-liquid interaction and efficient conversion of the syngas into methanol product. Unlike in cases where the micro gas bubbles are comprised of a non-reactive gas entering a vessel, and bubble coalescence. A non-reactive microbubble of gas would increase in size, a result of colliding with other bubbles, and would therefore rise faster through the fluid column. In this invention the micro syngas bubble is comprised of mostly hydrogen and carbon monoxide which are reactive and combine into a methanol molecule within a very short time once it enters the reactor. The micro syngas bubble collapses and becomes smaller and smaller as the syngas undergoes the transformation into methanol.

The reaction for methanol formation is strongly exothermic, creating a zone of higher temperature. In a solid catalyst, high temperatures cause the formation of hot spots within the solid catalyst bed, forming unwanted by-products and leading to carbon deposits on the catalyst surface and pores. The formation of by-products creates a costly step in the separation of methanol from the heat-related by-products. The liquid homogenous methanol producing catalyst absorbs the heat more effectively, and can be circulated out of the gas-liquid contact reactor and directed through a conduit into an external heat exchanger to remove the heat of reaction and moderate the overall temperature in the gas-liquid reactor. Efficient heat removal allows a more efficient rate of reaction within the gas-liquid contact reactor, reducing the production of unwanted by-products. Liquid catalyst eliminates the potential for carbon buildup and deactivation on the catalyst, leading to longer time on stream for higher production efficiencies.

Other embodiments of the present invention may include supplemental and/or alternative means of removing the heat of reaction, such as an internal cooling coil section immersed within the liquid within the gas-liquid contact reactor, or a cooling jacket on the outside of the gas-liquid contact reactor. The cooling coils or cooling jacket can be used to circulate a cooling fluid such as water or other suitable low temperature heat transfer fluid to remove the heat of reaction from within the reactor vessel thus moderating the reaction.

Returning now to FIG. 1, the remaining tail gas from the reactor vessel 20 rises to a conduit leading to condenser 22 where it is condensed at 60° F. (15° C.). Condensed methanol product is collected in tail gas separator 24 and sent to methanol storage, and the uncondensed gases are directed to a flare.

The remaining liquid catalyst solution from the reactor vessel 20 is pumped to the flash separator 30, which is maintained under a vacuum of −2 psig. Flash evaporation is one of the simplest liquid-liquid separation processes. A liquid stream containing two or more components is partially vaporized in a "flash drum" at a certain pressure and temperature. This results in two phases: a vapor phase, enriched in the more volatile component, primarily methanol, and a liquid phase, enriched in the less volatile catalyst solvent blend.

In various embodiments, the reactant fluid may be further pressurized by the transfer pump and/or further heated in line. It is then passed through a throttling valve or nozzle into the flash drum. The large drop in pressure causes the volatile components to vaporize. The vapor is taken off overhead, while the liquid drains to the bottom of the drum, where it is withdrawn and returned to the gas-liquid contact reactor. This type of system is called "flash" distillation because the vaporization is extremely rapid after the feed enters the drum. Because the intimate contact between the liquid and vapor, the system in the flash chamber is very close to equilibrium stage.

The methanol flash drum is configured as a vertical and/or horizontal vessel. As long as the feed consists of two components, there will be a binary flash. The continuous flash distillation and separating of the methanol from within the circulating reaction solvent fluid serves to further modulate the rise in fluid level within the gas-liquid contact reactor. The circulating rate is a function of the rate of production of methanol in the gas-liquid contact reactor. If too little methanol is flash separated from the fluid the level will rise in the gas-liquid contact reactor to unacceptable high level. If too much methanol is flash separated from the fluid level the fluid level the level will drop in the gas-liquid to unacceptable low level. Level sensors in the gas-liquid reactor chamber communicate with a process control device to regulate the rate of circulation.

The gas-liquid catalytic reaction of this invention has the advantage of providing a high single pass conversion of syngas into methanol. The high single pass efficiency eliminates the need for a method for recirculating the unreacted tail gas through gas conditioning and compression in order to maximize methanol production yield. It has been observed in lab pilot testing how a single pass conversion can reach over 85% conversion of syngas into methanol.

Returning now to FIG. 1, the methanol vapors separated from flash separator 30 are further condensed in condenser 32 at 60° F. (15° C.) and conveyed to separator 34, where the liquid methanol is conveyed methanol storage while any uncondensed gases are directed to vacuum pump 36 and on to flare.

A constant purge (drawing off of vapors) from flash separator 30 is directed to catalyst purge vessel 38, while the majority of the catalyst solution is recirculated through a heat exchanger 39 to cool the solution down to 120° F. (50° C.) before entering back into the reactor vessel 20. A flow of makeup catalyst 37 is also pumped in line to the methanol reactor to counter the solvent/catalyst losses in the process.

In the depicted embodiment, this process results in a continuous flowing volume of the liquid homogenous methanol conversion catalyst solvent solution, along with produced methanol, as they are removed from the reactor vessel 20 and pumped through an external heat exchanger to remove the heat of reaction, returning the liquid homogenous methanol conversion catalyst to the reactor vessel 20.

This use of a homogenous catalyst provides an easy means to reduce the heat of reaction, allowing for the low-pressure circulation of the catalyst-containing reaction fluid through a heat exchanger such as an external heat removal apparatus or air-cooled radiator. This provides a more economical and efficient means of controlling the catalyst solution temperature when compared to the traditional F-T process.

The circulating of the liquid from the gas-liquid contact reactor also allows for the returning liquid to be filtered removing unwanted solids which may form in the gas-liquid contact reactor which are the result of trace impurities in the syngas feed.

While various embodiments usable within the scope of the present disclosure have been described with emphasis, it should be understood that within the scope of the appended claims, the present invention can be practiced other than as specifically described herein.

The invention claimed is:

1. A system of continuously producing methanol from a syngas comprising:
   a gas sparger conveying syngas to a reactor chamber;
   a conduit conveying reactant fluid to the reactor chamber, wherein the reactant fluid comprises a liquid, homogenous catalyst;
   a first condenser receiving tail gas conveyed from the reactor chamber, wherein the first condenser precipitates liquid methanol from the tail gas, and wherein the first condenser conveys fluid to a first separator directing the liquid methanol to storage and uncondensed tail gas to a flare
   a flash separator receiving the combined reactant fluid from the reactor chamber, wherein the flash separator vaporizes methanol from the combined reactant fluid;
   a second condenser receiving methanol vapor from the flash separator, wherein the second condenser precipitates liquid methanol from the vapor, and wherein the second condenser conveys fluid to a second separator directing liquid methanol to storage and uncondensed gas to a flare; and
   a heat exchanger receiving the remaining reactant fluid from the flash separator, wherein the heat exchanger cools the reactant fluid and recirculates into the conduit conveying reactant fluid to the reactor chamber.

2. The system of claim 1, wherein the reactor chamber comprises an internal cooling coil immersed within the reactant fluid.

3. The system of claim 1, wherein the reactor chamber comprises an external cooling jacket circulating a cooling fluid.

4. The system of claim 1, wherein the reactor chamber comprises at least one level sensor, wherein the at least one level sensor regulates the activation of a pump conveying reactant fluid from the reactor chamber to the flash separator.

5. The system of claim 1, wherein the reactor chamber comprises a nozzle, an eductor assembly, a bubble-generating conduit, a bead-packed cylinder, or combinations thereof, to increase the gas-to-liquid surface area of the reaction.

6. The system of claim 5, wherein the syngas is conveyed to the lower half of the reactor chamber to increase the gas-to-liquid surface area of the reaction.

7. The system of claim 1, wherein the liquid homogenous catalyst comprises an organo-nickel compound, an ether solvent, an organic methoxide salt, or combinations thereof.

8. The system of claim 1, wherein the syngas production is enriched with up to a 90% oxygen concentration prior to syngas being treated and conveyed to the reactor vessel.

9. The system of claim 1, wherein the reactor chamber is maintained at a temperature between 100° C. and 200° C.

10. The system of claim 1, wherein the reactor chamber is maintained at a pressure of at least 1,000 kPa.

11. The system of claim 1, wherein the heat exchanger further comprises a filter removing solid impurities from the reactant fluid recovered from the flash separator.

12. The system of claim 1, wherein the conduit conveying the reactant fluid from the heat exchanger to the reaction chamber further comprises an in-line feed of makeup catalyst to replenish reaction losses.

* * * * *